United States Patent [19]

Mauldin et al.

[11] Patent Number: 4,977,126

[45] Date of Patent: Dec. 11, 1990

[54] PROCESS FOR THE PREPARATION OF SURFACE IMPREGNATED DISPERSED COBALT METAL CATALYSTS

[75] Inventors: Charles H. Mauldin; Kenneth L. Riley, both of Baton Rouge, La.

[73] Assignee: Exxon Research and Engineering Company, Florham Park, N.J.

[21] Appl. No.: 270,596

[22] Filed: Nov. 14, 1988

Related U.S. Application Data

[63] Continuation-in-part of Ser. No. 72,517, Jul. 13, 1987, abandoned, which is a continuation-in-part of Ser. No. 46,649, May 7, 1987, abandoned.

[51] Int. Cl.$^5$ ............... B01J 21/06; B01J 21/12; B01J 23/74; C07C 27/06
[52] U.S. Cl. ............... 502/242; 502/241; 502/260; 502/304; 502/325; 502/332; 502/350; 518/715
[58] Field of Search ............... 502/325, 304, 332, 335, 502/336, 241, 242, 260, 350

[56] References Cited

U.S. PATENT DOCUMENTS

| | | | |
|---|---|---|---|
| 2,599,978 | 6/1952 | Davis et al. | 502/325 |
| 2,865,868 | 12/1958 | McKinley et al. | 502/325 |
| 3,799,887 | 3/1974 | Brennan | 252/463 |
| 4,255,285 | 3/1981 | Engelbach et al. | 502/247 |
| 4,547,486 | 10/1985 | Shyr | 502/333 |
| 4,599,481 | 7/1986 | Post et al. | 585/700 |
| 4,637,993 | 1/1987 | Van Erp et al. | 502/242 |
| 4,729,981 | 3/1988 | Kobylinski et al. | 502/259 |
| 4,794,099 | 12/1988 | Iglesia et al. | 502/242 |

Primary Examiner—Paul E. Konopka
Attorney, Agent, or Firm—Jay Simon; L. A. Proctor

[57] ABSTRACT

A process for the preparation of catalysts wherein a catalytically effective amount of cobalt is impregnated and dispersed as a film, or layer, on the peripheral outer surface of a particulate porous inorganic oxide support, notably alumina, silica, silica-alumina and titania; particularly titania. The catalysts are prepared by spraying a bed of the fluidized particulate support particles with a liquid containing a dispersed or dissolved cobalt metal compound upon the support particles. The operation is performed at specified operating conditions.

13 Claims, No Drawings

PROCESS FOR THE PREPARATION OF SURFACE IMPREGNATED DISPERSED COBALT METAL CATALYSTS

CROSS REFERENCE TO RELATED APPLICATIONS

This application is a continuation-in-part of U.S. Ser. No. 072,517, now abandoned filed Jul. 13, 1987, which is a continuation-in-part of U.S. Ser. No. 046,649, now abandoned filed May 7, 1987.

FIELD OF THE INVENTION

This invention relates to a process for the preparation of cobalt catalysts wherein the metal is impregnated and dispersed as a thin film, or coating, on the peripheral or outside surface of a particulate carrier, or support, particularly a titania carrier, or support.

BACKGROUND OF THE INVENTION

Particulate catalysts are commonly employed in chemical, petroleum and petrochemical processing for chemically altering, or converting various gas and liquid feeds to more desirable products. Such catalysts are formed by dispersing a catalytically active metal, or metals, or the compounds thereof upon particulate carriers, or supports. In accordance with the conventional wisdom the catalytically active metal, or metals is generally dispersed as uniformly as possible throughout the particle, providing a uniformity of the catalytically active sites from the center of a particle outwardly.

Fisher-Tropsch synthesis, a process for the production of hydrocarbons from carbon monoxide and hydrogen (synthesis gas), has been commercially practiced in some parts of the world. This process may gain wider acceptance, perhaps in this country, if adequate improvements can be made in the existing technology. The earlier Fischer-Tropsch catalysts were constituted for the most part of non-noble metals dispersed throughout a porous inorganic oxide support. The Group VIII non-noble metals, iron, cobalt, and nickel have been widely used in Fischer-Tropsch reactions, and these metals have been promoted with various other metals, and supported in various ways on various substrates, principally alumina. Most commercial experience, however, has been based on cobalt and iron catalysts. The first commercial Fischer-Tropsch operation utilized a cobalt catalyst, though later more active iron catalysts were also commercialized. The cobalt and iron catalysts were formed by compositing the metal throughout an inorganic oxide support. The early cobalt catalysts, however, were of generally low activity necessitating the use of a multiple staged process, as well as low syn gas throughput. The iron catalysts, on the other hand, produce too much carbon dioxide from the synthesis gas with too little of the carbon monoxide being converted to hydrocarbons.

Cobalt catalysts of improved activity have nonetheless been made. For example, U.S. Pat. No. 4,542,122 by Payne et al, which issued Sept. 17, 1985, describes improved cobalt catalyst compositions useful for the preparation of liquid hydrocarbons from synthesis gas. These catalyst compositions are characterized, in particular, as cobalt-titania or thoria promoted cobalt-titania, wherein cobalt, or cobalt and thoria, is uniformly dispersed throughout the titania, or titania-containing support particles, especially a high rutile content titania. U.S. Pat. No. 4,568,663 by Mauldin, which issued Feb. 4, 1986, also discloses cobalt-titania catalysts to which rhenium is added to improve catalyst activity, and regeneration stability. In these catalysts both the cobalt and rhenium are uniformly dispersed throughout the support particles. In pending application Ser. No. 072,517, supra, there is described a cobalt catalyst, or catalyst wherein cobalt and an additional metal, or metals, e.g., rhenium, hafnium, zirconium, cerium, thorium, uranium or the like is dispersed as a thin film within a critical range of thicknesses on the peripheral, or outside surface of a particulate support, notably a titania or titania-containing support. These catalysts achieve high productivity, at low methane selectivity, in Fischer-Tropsch reactions. Productivity, which is defined as the standard volumes of carbon monoxide converted/volume catalyst/hour, is, of course, the life blood of a commercial operation. In the use of these catalysts, productivity in a Fischer-Tropsch reaction is considerably increased as contrasted with catalysts otherwise similar, employed at similar conditions, except that a similar metal, or metals, is uniformly dispersed throughout the particulate support. In application Ser. No. 072,517, data are given, and claim is made to forming catalysts by dispersing thin catalytically active surface layers of cobalt on heated support particles by repetitively spraying the particles with a solution of the cobalt compound.

OBJECTS

It is, accordingly, the primary objective of the present invention to provide further improvements in forming these high productivity Fischer-Tropsch cobalt catalysts via a process for impregnating by spraying a catalytically effective amount of cobalt, or cobalt and an additional metal, or metals, on the peripheral or outside surface of a particulate inorganic oxide support, particularly a particulate titania or titanium-containing support.

A further object is to provide a spray coating process, as characterized in the above-stated primary objective, wherein the cobalt, or cobalt and an additional metal, or metals, is sprayed, impregnated and dispersed upon the surface of said particulate support particles while the latter are maintained in heated condition and in a fluidized state.

A particular object of this invention is to provide a process for the preparation of cobalt catalysts, and promoted cobalt catalysts, useful in Fischer-Tropsch synthesis via use of a process for impregnating by spray coating a compound comprised of cobalt, or compounds comprised of cobalt and a promoter metal, or metals, on the peripheral or outside surface of a particulate inorganic oxide support, particularly a particulate titania or titanium-containing support, while the latter is maintained in heated condition and in a fluidized state.

A further, and more specific object is to provide a novel process for spray coating and impregnating cobalt, or cobalt and an additional cobalt modifier or promoter metal, or metals, on a heated fluidized particulate titania or titania-containing support, especially one wherein the titania or titania component has a high rutile:anatase ratio.

STATEMENT OF THE INVENTION

These objects and others are achieved in accordance with this invention embodying a process for the production of a catalyst wherein cobalt, or cobalt and an additional metal, or metals, catalytically effective in a Fischer-Tropsch synthesis reaction is coated as a catalytically active layer, or film, upon the peripheral or outside surface of a particulate porous inorganic oxide support by contacting and impregnating with a liquid dispersion, suitably a suspension or solution, of a compound of said metal, or metals, the support particles in a fluidized bed while the particles are maintained at temperature above about 50° C., preferably at temperature ranging from about 50° C. to about 100° C., and more preferably from about 70° C. to about 90° C. Preferred inorganic oxide supports are alumina, silica, silica-alumina and titania, and of these a titania or titania-containing support is most preferred; especially a rutile titania support, or support wherein the titania or titania component has a weight ratio of rutile:anatase of at least about 3:2. The catalytically active surface layer, or film, ranges in average thickness from about 20 microns to about 250 microns, preferably from about 40 microns to about 150 microns, with the loading of the cobalt expressed as the weight metallic cobalt per packed bulk volume of catalyst ranging from about 0.01 grams (g) per cubic centimeter (cc) to about 0.15 g/cc, preferably from about 0.03 g/cc to about 0.09 g/cc catalyst.

Metals such as rhenium, zirconium, hafnium, cerium, thorium and uranium, or the compounds thereof, can be added to cobalt to increase the activity and regenerability of the catalyst. Thus, the thin catalytically active layers, or films, formed on the surface of the support particles, especially the titania or titania containing support particles, can include in addition to a catalytically active amount of cobalt, any one or more of rhenium, zirconium, hafnium, cerium, thorium and uranium, or admixtures of these with each other or with other metals or compounds thereof. Preferred thin catalytically active layers, or films, supported on a support, notably a titania or a titania-containing support, thus include cobalt-rhenium, cobalt-zirconium, cobalt-hafnium, cobalt-cerium, cobalt-thorium and cobalt-uranium, with or without the additional presence of other metals or compounds thereof.

The support particles are fluidized in a bed and sprayed with a suspension, or solution containing a compound of cobalt, or a compound or compounds of cobalt and an additional metal, or metals, catalytically effective in a Fischer-Tropsch synthesis reaction. The temperature of the bed during spraying should be above 50° C., preferably from about 50° C. to about 100° C., and more preferably from about 70° C. to about 90° C. Suitably, the support particles are fluidized with a gas, preferably air, and the fluidized bed of support particles is sprayed with the suspension or solution via one or a plurality of nozzles. A key and novel feature of the process is that a very high particle drying capacity is generated during spraying by operating within a specified range of conditions of temperature and flow rate of the air, solution concentration of the metal, or metals, compound, or compounds, and flow rate of the suspension, or solution from the nozzle, or nozzles, into the bed. In forming a metal, or metals, film, or coating, of the required uniform thickness on the particulate particles, e.g., as in coating a cobalt metal film on a particulate titania support, the temperature of the bed during spraying, or spraying temperature, must be maintained at above about 50° C., and preferably from about 50° C. to about 100° C., and more preferably from about 70° C. to about 90° C., and the ratio of the solution feed rate to the fluidization gas, or air rate must be maintained below about 0.6 grams (g) solution per cubic feet (ft$^3$) of air, preferably from about 0.1 g/ft$^3$ to about 0.6 g/ft$^3$, and more preferably from about 0.3 g/ft$^3$ to about 0.5 g/ft$^3$. These parameters taken together provide high metals recovery, control the drying capacity, and generate catalysts with a uniform metal, or metals, film, or coating ranging in average thickness from about 20 microns to about 250 microns, preferably from about 40 to about 150 microns, with the loading of the metal, or metals, expressed as the weight metallic metal per packed bulk volume of catalyst ranging from about 0.01 g per cubic centimeter (cc) to about 0.15 g/cc, preferably from about 0.03 g/cc to about 0.09 g/cc catalyst. If the temperature of the fluidizing gas is on the higher side, then solution:gas ratios on the higher side of the expressed ranges are preferred; and conversely, if the temperature of the fluidizing gas is on the lower side, then solution:gas ratios on the lower side of the expressed ranges are preferred. The level of a metal, or metals, loading in the solution and the porosity of the support to some degree also effect the thickness of the metal, or metals, film, or coating, at a given set of spraying conditions. With cobalt, e.g., when operating within the expressed preferred range of conditions, the thickness of the cobalt film will range from about 100 microns to about 250 microns for a volumetric cobalt loading of about 6 g/100 cc.

In general, the concentration of the metal compound, or compounds, in the suspension or solution should be greater than about 5 wt. %, preferably 10 wt. %. Preferably a solution is employed, and the solution can be saturated or supersaturated with the metal compound, or metal compounds. The optimum concentration is probably best determined dependent upon the specific compound, or compounds employed. Low concentrations will require longer spraying time, and conversely high concentrations will decrease the spraying time. Balance between the specific solution concentration and period required for spraying for obtaining the required metal, or metals, loading on film thickness is required.

Several types of fluidizing bed apparatus are found in the literature, but the specific type and size of fluid bed device per se do not appear to have an effect on the depth of impregnation of the metal, or metals, below the peripheral surface of the particulate support. Known devices include, e.g., fluid bed granulator/dryers equipped with nozzles entering either above or below the bed, rotary granulators, and Wurster columns. Such devices are available at Glatt Air Techniques, Inc. of Ramsey, N.J., viz. a one-liter top sprayer (Versa-Glatt model) and a 20 liter top sprayer, Model GPCG-5, and at the Coating Place, Inc. of Verona, Wis., viz. a 20 liter bottom sprayer. Less breakage of the particles appears to occur with the top entering nozzle. Typically, in operating these units, the flow rate of the air is adjusted to that which is required to properly fluidize the support particles, and the rate of metals solution addition is then adjusted in relation to the flow rate of the air.

A cobalt-titania catalyst is particularly preferred. The cobalt-titania catalyst is one wherein the cobalt, or the cobalt and a promoter, is dispersed as a thin catalytically active film upon titania, or a titania-containing carrier, or support, in which the titania has a rutile:anatase weight ratio of at least about 3:2, as determined by ASTM D 3720-78: Standard Test Method for Ratio of Anatase to Rutile In Titanium Dioxide Pigments By Use of X-Ray Diffraction. Generally, the catalyst is one wherein the titania has a rutile:anatase ratio ranging at least about 3:2 to about 100:1, or greater, and more preferably from about 4:1 to about 100:1, or greater. Where any one of rhenium, zirconium, hafnium, cerium, thorium, or uranium metals, respectively, is added to the cobalt as a promoter to form the thin catalytically active film, the metal is added to the cobalt in concentration sufficient to provide a weight ratio of cobalt:metal promoter ranging from about 30:1 to about 2:1, preferably from about 20:1 to to about 5:1. Rhenium and hafnium are the preferred promoter metals, rhenium being more effective in promoting improved activity maintenance on an absolute basis, with hafnium being more effective on a cost-effectiveness basis. These catalyst compositions, it has been found, produce at high productivity, with low methane selectivity, a product which is predominately $C_{10}+$ linear paraffins and olefins, with very little oxygenates. These catalysts also provide high activity, high selectivity and high activity maintenance in the conversion of carbon monoxide and hydrogen to distillate fuels.

After the spraying is completed, the impregnated metal compounds must be decomposed to the corresponding metal oxides. Preferably, the catalyst is contacted with oxygen, air, or other oxygen-containing gas at temperature sufficient to oxidize the metal, or metals component, e.g., cobalt to convert the cobalt to $Co_3O_4$. Temperatures ranging above about 150° C., and preferably above about 200° C. are satisfactory to convert the metals, notably cobalt, to the oxide. Temperatures above about 500° C. are to be avoided. Suitably, the decomposition of the metal compound, or compounds, is achieved at temperatures ranging from about 150° C. to about 300° C. The decomposition step can be conducted in the fluidized bed device or in an external oven, or calcination device.

Cobalt catalysts produced by the process of this invention have proven especially useful for the preparation of liquid hydrocarbons from synthesis gas at high productivities, with low methane formation. They contain essentially all of the active metal, notably cobalt, on the outer peripheral surface of the support particles, while the metal is substantially excluded from the inner surface of the particles. The high metal, or metals, loading in a thin rim, or shell, on the outer surface of the particles maximizes reaction of the hydrogen and carbon monoxide at the surface of the catalytic particle. This avoids the normal diffusion limitation of most prior art catalysts, the catalyst behaving more ideally, approaching the behavior of a powdered catalyst which is not diffusion limited. However, unlike in the use of powdered catalysts the flow of the reactants through the catalyst bed, because of the larger particle size of the catalyst, is virtually unimpeded. The production of this type of catalyst on a large scale, while very difficult if at all feasible by known techniques, is readily accomplished via the process of this invention.

In conducting synthesis gas reactions the total pressure upon the CO and $H_2$ reaction mixture is generally maintained above about 80 psig, and preferably above about 140 psig. It is generally desirable to employ carbon monoxide, and hydrogen, in molar ratio of $H_2$:CO above about 0.5:1 and preferably equal to or above about 1.7:1 to increase the concentration of $C_{10}+$ hydrocarbons in the product. Suitably, the $H_2$:CO molar ratio ranges from about 0.5:1 to about 4:1, and preferably the carbon monoxide and hydrogen are employed in molar ratio $H_2$:CO ranging from about 1.7:1 to about 2.5:1. In general, the reaction is carried out at gas hourly space velocities ranging from about 100 V/Hr/V to about 5000 V/Hr/V, preferably from about 300 V/Hr/V to about 1500 V/Hr/V, measured as standard volumes of the gaseous mixture of carbon monoxide and hydrogen (0° C., 1 Atm.) per hour per volume of catalyst. The reaction is conducted at temperatures ranging from about 160° C. to about 290° C., preferably from about 190° C. to about 260° C. Pressures preferably range from about 80 psig to about 600 psig, more preferably from about 140 psig to about 400 psig. The product generally and preferably contains 60 percent, or greater, and more preferably 75 percent, or greater, $C_{10}+$ liquid hydrocarbons which boil above 160° C. (320° F.).

The invention will be more fully understood by reference to the following examples and demonstrations which present comparative data illustrating its more salient features. All parts are in terms of weight units except as otherwise specified.

EXAMPLES 1-10

A series of supports, for use in preparing catalysts, were obtained from reliable commercial sources or prepared from particulate titania-alumina (96.5% Ti/3.5% $Al_2O_3$), silica, and alumina, both in extrudate and spherical form. The identity of the supports, their physical size and form, and certain physical characteristics—viz. surface area (S.A.) in square meters per gram (B.E.T.), pore volume (PV) as measured by mercury intrusion, and porosity are given in Table 1.

TABLE 1

| Support Number | Composition | Form | SA, $m^2/g$ | PV, cc/g | Porosity |
|---|---|---|---|---|---|
| I | 96.5% $TiO_2$/ 3.5% $Al_2O_3$ | 0.8 mm Extrudates | 15 | 0.27 | 0.54 |
| II | 96.5% $TiO_2$/ 3.5% $Al_2O_3$ | 0.8 mm Extrudates | 51 | 0.42 | 0.64 |
| III | 96.5% $TiO_2$/ 3.5% $Al_2O_3$ | 0.8 mm Extrudates | 3 | 0.21 | 0.49 |
| IV | $SiO_2$ | 2.4 mm Spheres | 244 | 1.23 | 0.74 |
| V | $Al_2O_3$ | 0.8 mm Extrudates | 288 | 0.43 | 0.56 |

The catalysts made from these supports are described in Table 2, the support employed in the catalyst preparation being identified by the support number related back to Table 1.

Aqueous solutions of cobalt nitrate (11-13 wt. % Co) and perrhenic acid (1-1.3 wt. % Re) were used in the preparation of a series of 15 catalysts. These catalysts were individually prepared in fluid bed sprayers, the Glatt Air Techniques, Inc. 1-liter and 20-liter top sprayers, respectively, and 20-liter bottom sprayer supplied by Coating Place, Inc. The catalysts were calcined as designated in Table 2. Table 2 also lists the weight of the charge to the fluid bed sprayer, the solution rate in g/minute, the fluidizing air rate in $ft^3$/minute (CFM), solution:air ratio in $g/ft^3$, the average bed temperature during spraying, the method of calcination, the wt. % Co-Re on the finished catalyst and the average depth from the outer surface, or thickness of the Co-Re on the outer surface of the support particles in microns, viz. RIM thickness, as measured by an electron probe analyzer (produced by JEOL Company, Model No. JXA-50A). The thickness of the Co-Re surface layer, or RIM, is a measure of the success, or lack of success, of a given catalyst preparation. Metal distribution was not found to be uniform across this depth; the concentration often decreasing with increased distance from the peripheral surface of the particles. The depth within a particle, and measurements made from particle to particle however generally showed good uniformity; particularly as regards Catalyst Preparation Nos. 1 through 10, inclusively, which were successful in accordance with this invention. In addition to average RIM thickness, metals recovery is also an important criteria for success, metals recovery exceeding over 90 wt. % except as regards Example 12.

Preparations 7 and 8 show that RIM thickness is a function of support porosity. The RIM is thinner (preparation no. 7 vs preparation no. 4a) when the support has a higher pore volume. The RIM is much thicker (preparation no. 8 vs preparation nos. 4a, 7) when low pore volume is present.

Preparations 9 and 10 demonstrate success with silica and alumina supports.

Preparations 11 and 12 show the adverse effects of operating outside the preferred temperature range. Preparation no. 11 shows that spraying below 50° C. does not give a RIM, in spite of using a low solution:air

TABLE 2

| Catalyst Preparation No. | Support No. | Sol'n Rate, kg g/min | Fluidiz. Air Rate CFM | Sol'n: Air Ratio g/ft | Avg. Bed Temp. °C. | Calcin. Meth.[1] | Wt. % Co | RIM Thickness Microns |
|---|---|---|---|---|---|---|---|---|
| 1 | I | 1.0 | 21 | 56 | 0.38 | 95 | B | 4.5 | 123 |
| 2 | I | 1.0 | 21 | 76 | 0.28 | 73 | B | 4.6 | 203 |
| 3 | I | 15.0 | 50 | 150 | 0.33 | 61 | B | 4.2 | 254 |
| 4a | I | 22.0 | 187 | 335 | 0.56 | 89 | A | 4.2 | 166 |
| 4b | I | 22.0 | 187 | 335 | 0.56 | 89 | B | 4.2 | 240 |
| 5 | I | 1.0 | 19 | 64 | 0.30 | 72 | C | 2.0 | 105 |
| 6 | I[3] | 0.9 | 19 | 62 | 0.31 | 69 | B | 3.8 | 114 |
| 7 | II | 0.8 | 19 | 55 | 0.35 | 84 | B | 4.6 | 115 |
| 8 | III | 1.3 | 19 | 49 | 0.39 | 82 | B | 2.9 | 290 |
| 9 | IV | 0.4 | 19 | 65 | 0.29 | 73 | B | 7.7 | 118 |
| 10 | V | 0.6 | 20 | 57 | 0.35 | 70 | B | 6.9 | 153 |
| 11 | I | 1.0 | 15 | 57 | 0.26 | 40 | B | 2.8 | Even |
| 12 | I | 22.0 | 165 | 375 | 0.44 | 110 | A | 2.7 | 119 |
| 13 | I | 1.0 | 45 | 46 | 0.98 | 51 | B | 4.5 | Even |
| 14 | I | 22.0 | 294 | 375 | 0.78 | 88 | A | 4.7 | 298 |

[1]Calcination Methods:
A = 220° C. in Sprayer
B = 300° C. in Tube Unit
C = 250° C. in Oven
[2]Only 60% of Cobalt Deposited on Catalyst
[3]Catalyst preparation no. 6 was made by depositing additional metal onto the catalyst made in preparation no. 5

The following conclusions can be drawn from the preparations described in Table 2, to wit:

Preparations nos. 1-4a illustrate the strong relationship of spraying temperature to RIM thickness, with other conditions being relatively constant. The higher the temperature, over the range from 50°-100° C., the thinner the RIM. Note that preparation nos. 1-3 were sprayed at a low solution:air ratios.

Preparations 4a and 4b show that RIM thickness is dependent to an extent on the final calcination step. The molten nitrate salt migrates further into the support during the heat-up, before it decomposes to the oxide. The migration of the metals toward the center of the particles can be minimized by quick heat-up, and the sprayer provides the best way to do this. An alternative approach is to use low solution:air ratio during spraying. The extra drying this affords helps minimize the tendency of the RIM to migrate later during the calcination. The solution:air ratio of 0.56 is at the high end of the acceptable range. The RIM increased significantly when a small portion was withdrawn from the sprayer immediately after spraying, and then calcined in a tube unit.

Preparation no 5, compared to preparation no 2, shows that RIM thickness is a function of cobalt loading. The less cobalt sprayed onto the support, the thinner the RIM at constant spray conditions.

Preparation no. 6 shows that exceptionally thin RIMs can be made at high metal loadings. In this case preparation no. 5 was simply returned after calcining to the sprayer for another impregnation. A very thin RIM resulted compared to a single impregnation, preparation no. 2.

ratio and depositing only 2.8% cobalt. Preparation no. 12 shows that spraying at 110° C. gives a thin RIM but only 60% of the metal sprayed ended up on the catalyst. The rest of the cobalt and expensive rhenium were carried out overhead as fines. "Spray drying" of the solution and decomposition of the nitrate appear to have occurred before the solution reached the support.

Preparations 13 and 14 show that good RIMs are not obtained when high solution:air ratios are used.

Further, to demonstrate the utility of these RIM catalysts, a series of Fischer-Tropsch runs were made with the catalysts which had been successfully prepared by the fluid bed technique. All were successful, and the data obtained agreed well with the predicted performance based on the cobalt loading and RIM thickness of each catalyst preparation. The results obtained with catalyst preparation 4a can be considered illustrative. Thus, preparation no. 4a was used to convert synthesis gas to heavy hydrocarbons. A portion of the catalyst was reduced at 450° C. for 1 hour and then reacted with a feed containing 65% $H_2$/31% CO/4% Ne at 200° C., 280 psig, GHSV=1000. CO conversion was 79% after 20 hours operation. Product selectivity, in terms of moles of CO converted to a product per moles of CO reacted, was: 6.0% $CH_4$, 0.4% $CO_2$, and 93.6% $C_2+$.

It is apparent that various modifications and changes can be made without departing the spirit and scope of the present invention.

Having described the invention, what is claimed is:

1. In a process for the production of catalysts wherein a catalytically effective amount of cobalt is impregnated and dispersed on the outer surface of a particulate porous inorganic oxide support to form a catalyst useful for the conversion of synthesis gas to hydro-carbons, and the support particles are contacted with a spray containing a decomposable compound of cobalt, the improvement comprising maintaining a bed of the support particles in a fluidized state at temperature ranging from about 50° C. to about 100° C. by contact with a gas at temperature ranging from about 50° C. to about 100° C., spraying the bed of the heated support particles with a liquid in which a cobalt compound is dispersed at flow rate sufficient to provide a ratio between the flow rate of the liquid: flow rate of the fluidizing gas below about 0.6 grams liquid/ft$^3$ of fluidizing gas to form on the particles a surface layer of cobalt compound in average thickness ranging from about 20 microns to about 250 microns, with the loading of cobalt compound ranging from about 0.01 g/cc to about 0.15 g/cc, calculated as metallic cobalt per packed bulk volume of catalyst.

2. The process of claim 1 wherein the ratio of the flow rate of the liquid:flow rate of the fluidizing gas ranges from about 0.3 g/ft$^3$ to about 0.5 g/ft$^3$.

3. The process of claim 1 wherein the spray liquid contains an additional decomposable promoter metal compound the metal being selected from the group consisting of rhenium, hafnium, zirconium, cerium, thorium, uranium, and mixtures thereof, and cobalt compound is dispersed and impregnated with said additional metal compound as a surface layer on said support, the weight ratio of cobalt:promoter of about 30:1 to about 2:1.

4. The process of claim 1 wherein the catalytically active surface layer of the catalyst is of average thickness ranging from about 40 microns to about 150 microns with the cobalt loading ranging from about 0.03 g/cc to about 0.09 g/cc.

5. The process of claim 1 wherein the support is comprised of alumina, silica, silica-alumina, titania or admixtures comprised of alumina, silica or titania.

6. The process of claim 5 wherein the support is comprised of titania.

7. The process of claim 6 wherein the titania has a rutile:anatase weight ratio of at least about 3:2.

8. The process of claim 7 wherein the titania has a rutile:anatase weight ratio ranging at least about 3:2 to about 100:1, and higher.

9. The process of claim 1 wherein the liquid within which the compound, or compounds, of cobalt is dispersed is water.

10. The process of claim 1 wherein the fluidizing gas is air.

11. The process of claim 1 wherein the temperature of the fluidizing gas ranges from about 70° C. to about 90° C.

12. The process of claim 11 wherein the fluidizing gas is air.

13. The process of claim 1 wherein the cobalt compound is converted to cobalt oxide at temperatures below about 500° C.

* * * * *